US009155822B2

(12) United States Patent
Woo et al.

(10) Patent No.: US 9,155,822 B2
(45) Date of Patent: Oct. 13, 2015

(54) VENTRICULAR ASSIST DEVICE SLEEVE ADAPTER

(71) Applicant: The Trustees of the University of Pennsylvania, Philadelphia, PA (US)

(72) Inventors: Y. Joseph Woo, Lafayette Hill, PA (US); Pavan Atluri, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/294,880

(22) Filed: Jun. 3, 2014

(65) Prior Publication Data

US 2014/0288353 A1    Sep. 25, 2014

Related U.S. Application Data

(63) Continuation of application No. PCT/US2012/066921, filed on Nov. 29, 2012.

(60) Provisional application No. 61/568,866, filed on Dec. 9, 2011.

(51) Int. Cl.
*A61N 1/362* (2006.01)
*A61M 1/12* (2006.01)
*A61M 1/10* (2006.01)

(52) U.S. Cl.
CPC ............... *A61M 1/122* (2014.02); *A61M 1/10* (2013.01); *A61M 1/1008* (2014.02)

(58) Field of Classification Search
CPC ..... A61M 1/1068; A61M 1/106; A61M 1/10; A61M 1/12; A61M 1/22
See application file for complete search history.

(56) References Cited

U.S. PATENT DOCUMENTS

| 4,048,990 | A | | 9/1977 | Goetz |
| 4,690,134 | A | * | 9/1987 | Snyders ..................... 601/153 |
| 4,955,856 | A | | 9/1990 | Phillips |
| 6,732,501 | B2 | | 5/2004 | Yu et al. |
| 7,628,808 | B2 | | 12/2009 | Schmid et al. |
| 2002/0095210 | A1 | | 7/2002 | Finnegan et al. |

OTHER PUBLICATIONS

International Search Report and Written Opinion for PCT/US2012/066921, dated Mar. 5, 2013.

* cited by examiner

*Primary Examiner* — Robert N Wieland
(74) *Attorney, Agent, or Firm* — Baker Botts, LLP (57) ABSTRACT

A sleeve adapter for connecting a ventricular assist device to a ventricle of the heart.

18 Claims, 6 Drawing Sheets

VENTRICULAR ASSIST DEVICE SLEEVE ADAPTER

CROSS REFERENCE TO RELATED APPLICATION

This application is a continuation of International Application PCT/US12/066921, filed on Nov. 29, 2012, which claims priority to U.S. Provisional Patent Application Ser. No. 61/568,866, filed Dec. 9, 2011, the contents of which are hereby incorporated by reference in their entirety and from which priority is claimed.

FIELD OF THE INVENTION

The present invention is directed to adapters that allow a surgeon to attach a damaged heart ventricle to a ventricular assist device.

BACKGROUND OF THE INVENTION

Heart Failure, often called congestive heart failure, is a condition in which the heart can no longer pump sufficient blood to the rest of the body. Heart failure is a major health problem in the U.S. with hundreds of thousands of cases diagnosed each year. There are a variety of causes for heart failure. The most common cause is coronary artery disease, which is a narrowing of the small blood vessels that supply blood and oxygen to the heart. Other causes of heart failure include congenital heart disease, heart attacks, heart valve diseases and abnormal heart rhythms (arrhythmias).

A variety of surgeries and devices have been developed to treat patients with heart failure, including coronary bypass surgery, angioplasty, heart valve surgery, addition of a pacemaker, or installation of a defibrillator. When treatments no longer work, a patient is said to be in end-stage heart failure. For patients in end-stage heart failure, a heart transplant is often the only possible treatment option. Unfortunately, there is a serious shortage of donors. The annual number of donor hearts remains around 2,000. However, the patients who are qualified to receive and need donor hearts is estimated to be about 16,500. To compensate for this lack of donor hearts, mechanical circulation support systems have been intensively studied and developed. Such mechanical circulation support systems include artificial hearts and ventricular assist devices.

Figure 1:
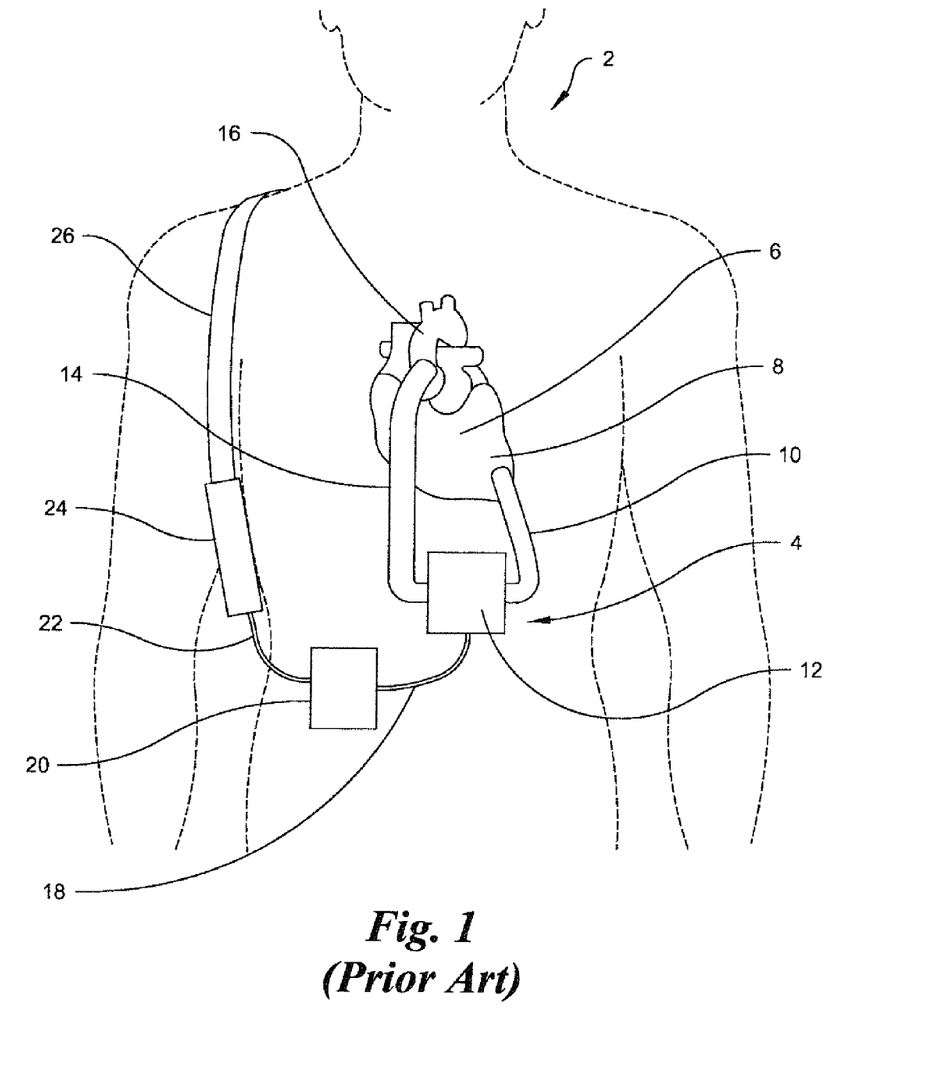
FIG. 1 shows a patient with an implanted ventricular assist device.

A ventricular assist device (VAD) is a mechanical pump that helps a ventricle to pump blood throughout the body. The VAD pumps the blood from a weakened or diseased ventricle to the aorta or a pulmonary artery. The components of a VAD vary according to the specific device used. In general, a VAD includes a pump, connections to and from the heart, a control system and an energy supply. A general representation of a ventricular assist device is presented in FIG. 1. Referring now to FIG. 1, a patient 2 is shown with an implanted VAD 4 in the body of the patient 2. The patient's heart 6 includes the left ventricle 8 which is attached to a ventricle tube 10 which enters the left ventricle 8. The ventricle tube 10 is attached to a pump 12. A variety of pumps are used in VADs, including rotary and axial flow pumps. The pump 12 pumps blood from the left ventricle 8 into a pump exit tube 14 which delivers the blood to the aorta 16. The pump 12 has a control unit wire 18 which is attached to the pump 12 and which exits the patient's body 2 and is attached to a control unit 20. The control unit 20 controls the action of the pump 12 and is attached to a power unit wire 22 which attaches to a power unit 24 which powers the pump 12. A power unit 24 may be battery charged or may plug into a power source such as a wall outlet. A variety of means are available to carry the power unit 24, such as a sling 26. In some instances a VAD is used to keep the patient alive until a donor heart is available. Such use is referred to as a "bridge to transplant." In "destination therapy" a VAD is used in place of a heart transplant to provide a long-term solution for patients that are not eligible for a heart transplant.

There are situations where a patient needs a VAD, but the ventricle in need of the VAD is diseased or otherwise damaged in a way that makes attachment of the VAD to the ventricle difficult or impossible. The present invention is directed to sleeve adapter and methods for connecting a VAD to a damaged or diseased ventricle thereby greatly expanding the number of patients able to receive a VAD.

SUMMARY OF THE INVENTION

The present invention relates to a sleeve adapter for connecting a ventricular assist device to a ventricle of a heart having a ventricular surface. The sleeve adapter comprises a flexible substrate having an opening therethrough and a sleeve outlet extending axially through the opening in the substrate. The sleeve outlet has first and second ends oppositely disposed and the substrate is sealingly attached to the sleeve outlet. The substrate is adapted for sealing attachment to the ventricular surface, the first end of the sleeve outlet facing the ventricle, the second end of the sleeve outlet projecting outwardly from the ventricle and being connectable in fluid communication with the ventricular assist device. In one embodiment, the substrate has a conical shape. The conical shaped embodiment may have a lip defining an opening. In one embodiment the lip is elliptical.

In yet another embodiment of the sleeve adapter, the substrate is sealingly attached to the sleeve outlet at one end or may be sealingly attached to the sleeve outlet between the first and second ends of the sleeve outlet.

In certain embodiments of the sleeve adapter, the substrate is made from a material selected from the group consisting of polytetrafluoroethylene (PTFE), gelatin sealed grafts, antibiotic treated grafts, velour, Gore-Tex, polyethylene terephthalate (Dacron®), silk and combinations thereof, and the sleeve outlet is made from material selected from the group consisting of Dacron®, polytetrafluoroethylene (PTFE), gelatin sealed grafts, antibiotic treated grafts, velour, Gore-Tex, polyethylene terephthalate (Dacron®), silk and combinations thereof.

Embodiments of the sleeve adapter may further comprise a rib attached to the substrate. In one embodiment the ribs may be detached from the substrate. The rib can extend helically or circumferentially around the substrate or in conical embodiments, the rib may extend lengthwise along the substrate.

In certain embodiments of the sleeve adapter, the substrate may also include markings to facilitate cutting the substrate to a desired size.

In yet another embodiment, the sleeve adapter comprises a flexible substrate having an opening, and an attachment gasket sealingly attached to the opening in the substrate, the attachment gasket being connectable in fluid communication with the ventricular assist device.

The sleeve adapter may also comprise sutures extending between the sleeve outlet and the substrate for attaching the substrate to the sleeve outlet.

The sleeve adapter may also comprise sutures extending between the substrate and the ventricle for attaching the substrate to the ventricle.

In an embodiment for use with both the left and right ventricles, the ventricles having ventricle surfaces, the substrate has a second opening therethrough and a second sleeve outlet in a spaced relation from the sleeve outlet, the second sleeve outlet extending through the substrate, the second sleeve outlet having first and second ends oppositely disposed, the substrate being sealingly attached to the second sleeve outlet and the second sleeve outlet projecting outward from a ventricle and being connectible in fluid communication with the ventricular assist device. This embodiment includes a plenum attached to the interior surface of the substrate wall, the plenum dividing the substrate into a first chamber and a second chamber, the first chamber sealingly attachable to the left ventricle, and the second chamber sealingly attachable to the right ventricle.

BRIEF DESCRIPTION OF THE DRAWINGS

The invention is illustrated with the following Figures in which similar reference numbers used in different Figures denote similar components wherein.

DETAILED DESCRIPTION OF THE INVENTION

The present invention relates to a sleeve adapter for connecting a ventricular assist device (VAD) to the ventricle of the heart. In some situations a patient's ventricle may be damaged to the point where it is very difficult or impossible to attach the ventricle tube of a VAD using normal procedures because the surgeon may have had to cut away a portion of the damaged ventricle. For example, the apex of the ventricle may be calcified, brittle, friable, or very thin requiring a partial ventriculectomy to remove a portion of the ventricle. The present sleeve adapter provides the ability to attach the ventricle tube of a VAD to such damaged ventricles.

In particular, the present invention provides a sleeve adapter for attaching a VAD to such damaged ventricles, making it possible to implant VADs in patients that previously would have been ruled out as recipients for a VAD. The sleeve adapter is made of materials which are biocompatible and are able to withstand the pressures created by the heart, the VAD pump and compression forces in the body due to movement by the patient.

A wide variety of different VADs sold by various manufacturers may be used with the present sleeve adapter including left ventricle VADs, right ventricle VADS, and left and right ventricle VADs. Examples of VADs include the HeartMate II Left Ventricular Assist Device, the Paracorporeal Ventricular Assist Device (PVAD), and the Implantable Ventricular Assist Device (IVAD), sold by Thoratec, and the HeartWare Ventricular Assist System, sold by HeartWare International Inc. In a preferred embodiment, the present sleeve adapter is used to attach a left ventricular assist device (LVAD) to the left ventricle of the heart.

Figure 2:
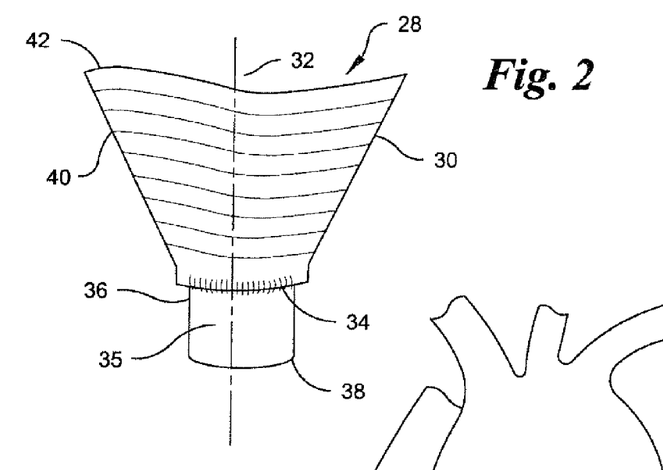
FIG. 2 is an elevational view of the sleeve adapter having a conical shape and markings on the substrate.

The sleeve adapter may be prepared in a variety of shapes, including but not limited to a conical shape. FIG. 2 illustrates an embodiment of the sleeve adapter 28, having a conical shape. The sleeve adapter 28 includes a flexible substrate 30 which is acceptable for long-term presence in the human body without immunological or other pathological effects including infection. The substrate 30 is made of material strong enough to be attached to the heart by sutures or other surgical attachment means and is able to withstand the forces encountered in the body due to the pressures created by the pump, the heart and compression forces encountered in the patient's chest cavity due to movement of the patient. The substrate 30 may be made from materials which are sufficiently biocompatible and strong enough to remain attached to the ventricle for the life of the patient. A variety of materials may be used to make the substrate 30 such as, polytetrafluoroethylene (PTFE), gelatin sealed grafts, antibiotic treated grafts, velour, Gore-Tex, polyethylene terephthalate (Dacron®), and silk. Antibiotic treated grafts may include any suitable antibiotic such as, but not limited to, rifampin.

The substrate 30 has a longitudinal axis 32 which includes an opening 34 which is located approximately in the center of the substrate 30, although in certain embodiments it may be desirable to position the opening 34 off-center. A sleeve outlet 35 extends axially through the opening 34. A variety of materials may be used to make the sleeve outlet, including polytetrafluoroethylene (PTFE), gelatin sealed grafts, antibiotic treated grafts, velour, Gore-Tex, polyethylene terephthalate (Dacron®), and silk. The sleeve outlet 35 has a first end 36 and a second end 38, which are oppositely disposed. The substrate 30 is attached to the sleeve outlet 35 at the first end 36 of the tube or between the first end 36 and second end 38 of the sleeve outlet 35. The second end 38 of the sleeve outlet 35 projects outwardly from the ventricle when attached to the heart and provides a fluid-tight connection with the VAD.

In certain embodiments the substrate 30 can have markings 40, preferably circumferential markings, to allow for appropriate sizing by the surgeon during attachment to the ventricle. The surgeon may use these markings for guidance in cutting away portions of the substrate 30 to obtain the correct size of the sleeve adapter 28 needed to make a fluid tight attachment of the sleeve adapter 28 to the ventricle. The amount of the substrate 30 that may be cut away may vary given how much of the ventricle has been removed or is damaged. The marking 40 may be of any desired unit of length such as centimeters, for example the markings may be placed 1 centimeter apart from one another. The thickness of the substrate 30 can vary and can be from about 0.1 to about 5 mm thick. The substrate has a lip 42 which facilitates attachment of the adapter 28 to the heart.

Figure 3:
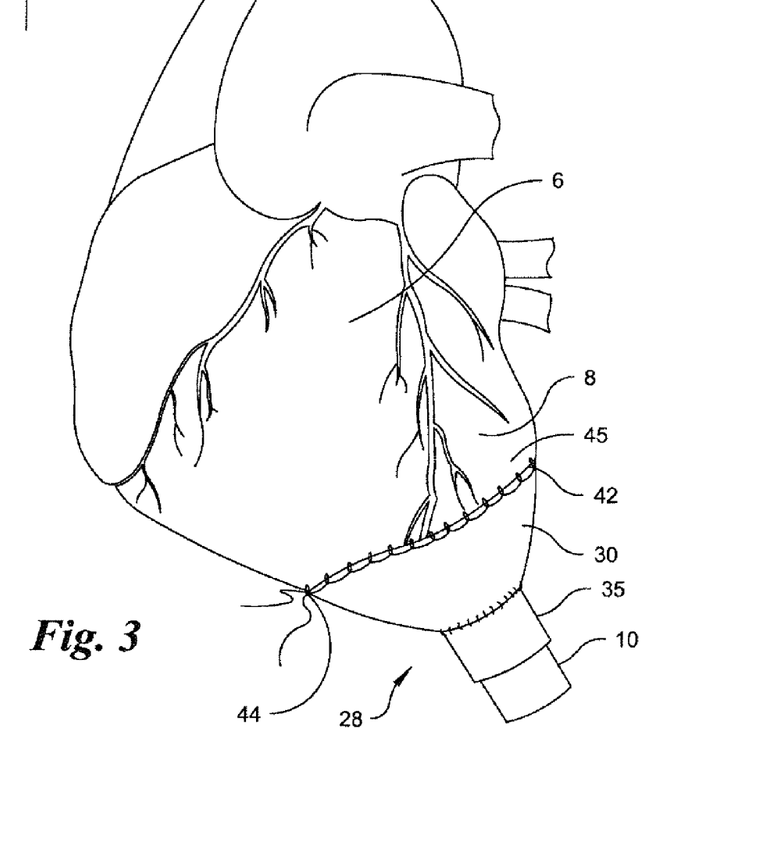
FIG. 3 is an elevational view of the sleeve adapter of FIG. 2 attached to the left ventricle of the patient's heart.

Referring now to FIG. 3, the conical shaped sleeve adapter 28 of FIG. 2 is shown attached to the heart 6. In particular, the lip 42 of the substrate 30 is attached by surgical attachment means 44 to the left ventricular surface 45 of the ventricle 8 of the heart 6. The surgical attachment means 44 position and anchor the sleeve adapter 28 to the patient's left ventricle 8. A variety of surgical attachment means may be used in the practice of the invention, including surgical sutures. The term "suture" refers to using materials to close a wound or opening in the body typically using a nonabsorbable polyester thread. The sutures may be made of synthetic material such as polyglycolic acid, polylactic acid, polydioxanone, nylon or polypropylene and may be coated with antimicrobial substances to reduce the chances of wound infection. The surgeon may also use "pledgets," which are small flat pads made out of artificial biocompatible materials, fixed biologic tissues, or autologous human tissue used to protect a wound and/or assist in the attachment of the sleeve adapter 28 to the heart 6. A variety of materials may be used to make a pledget including PTFE coated felt. If desired, the surgeon may also use an appropriate bioglue to attach the sleeve adapter. Such bioglues can include cyanoacrylate based fast-acting glues such as methyl-2-cyanoacrylate, ethyl-2-cyanoacrylate, n-butyl-cyanoacrylate, or 2-octyl cyanoacrylate. The ventricle tube 10 which is in fluid attachment with the pump of the VAD is introduced into the sleeve outlet 35 and the sleeve outlet 35 is secured in fluid tight attachment around the ventricle tube 10 so that blood does not leak from the site of attachment of the ventricle tube 10 to the sleeve outlet 35. Following this attachment of the ventricle tube 10, blood can travel from the left ventricle to the pump of the VAD.

Figure 4:
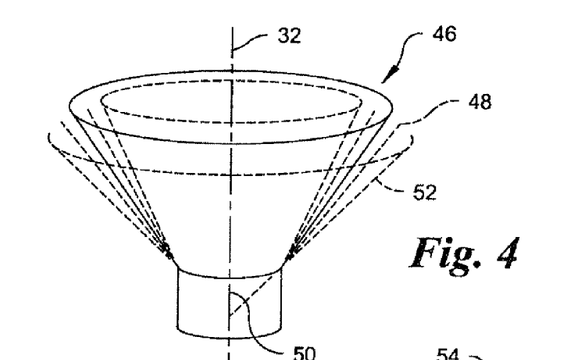
FIG. 4 is an isometric view of the sleeve adapter illustrating the sleeve adapter may be made in a variety of sizes.

In addition to different size sleeve adapters FIG. 4 represents a conical embodiment 46 of the sleeve adapter illustrating that the sleeve adapter 46 can be made with a variety of different conical angles. Dotted lines 48 illustrate that the sleeve adapter 46 can have a variety of different cone angles described by angle 50, formed between the longitudinal axis 32 of the sleeve adapter and the substrate wall 52. The angle can be from about 0° to about 90°. A surgeon can select the best angle of a premanufactured embodiment of the sleeve adapter 46 given the size of the ventricle that needs to be covered.

Figure 5:
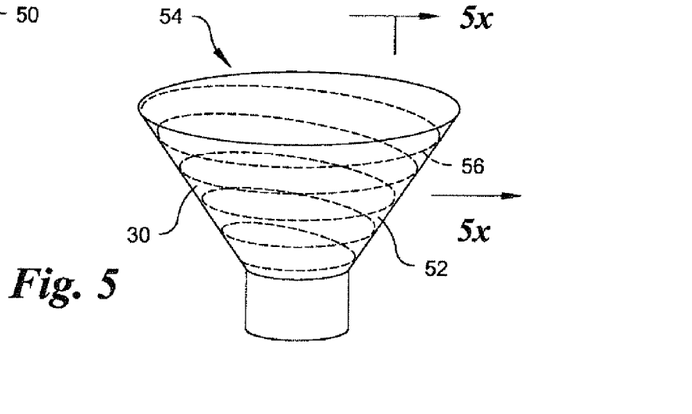
FIG. 5 is an isometric view of the sleeve adapter with a helical rib support.
Figure 5A:
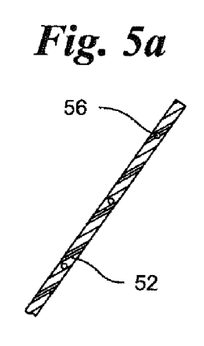
FIG. 5a is a cross sectional view taken along lines 5x showing a rib in the wall of the sleeve adapter.
Figure 5B:
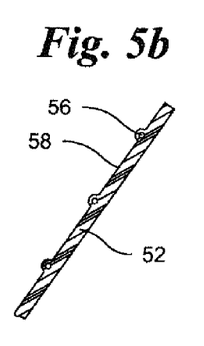
FIG. 5b is a cross sectional view taken along lines 5x showing a rib on the inside wall of the sleeve adapter.
Figure 5C:
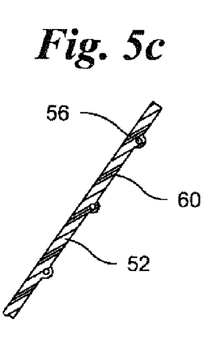
FIG. 5c is a cross sectional view taken along lines 5x showing a rib on the outside wall of the sleeve adapter.

FIG. 5 shows a sleeve adapter 54 with a rib 56 attached to the substrate 30. The rib 56 may be made of any material that can retain its shape after minor distortion, including, but not limited to, metals and alloys such as nintinol, stainless steel, titanium and various polymers and fabric materials. The rib 56 extends helically around the substrate 30. As shown along lines 5x the ribs 56 may be positioned within the substrate wall 52 (FIG. 5a) or in the interior surface of the substrate wall 58 (FIG. 5b) or exterior surface 60 (FIG. 5c) of the substrate wall. The rib 56 provides structural support to the sleeve adapter to resist distortion and/or collapse of the sleeve adapter during use. In certain situations it may be desirable to use ribs which may be detached from the substrate 30. The ribs may utilize any suitable means of attachment to the substrate such as a biocompatible adhesive material. A surgeon may detach unneeded ribs or alternatively, attach additional ribs to further support the sleeve adapter based on the condition of the ventricle.

Figure 6:
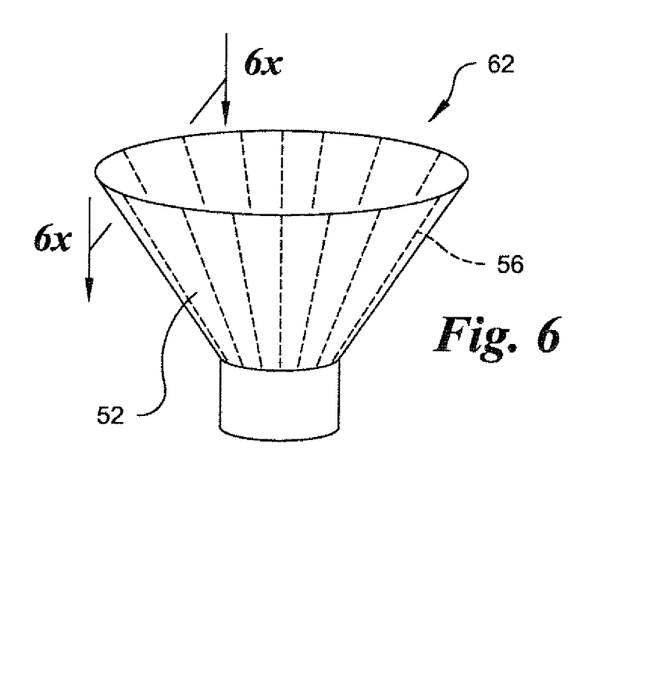
FIG. 6 is an isometric view of the sleeve adapter with horizontal support rib support.
Figure 6A:
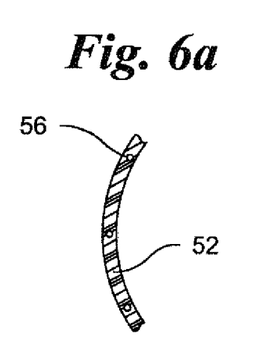
FIG. 6a is a cross sectional view taken along lines 6x showing a rib in the wall of the sleeve adapter.
Figure 6B:
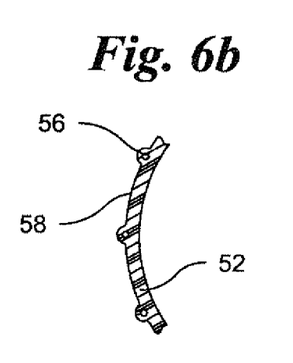
FIG. 6b is a cross sectional view taken along lines 6x showing a rib on the inside wall of the sleeve adapter.
Figure 6C:
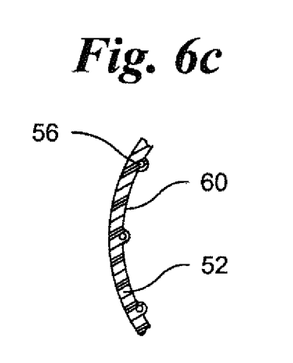
FIG. 6c is a cross sectional view taken along lines 6x showing a rib on the outside wall of the sleeve adapter.

FIG. 6 represents yet another conical embodiment 62 with ribs 56. These ribs 56 extend lengthwise along the cone. As shown along lines 6x these ribs 56 may be located within the substrate wall 52 (FIG. 6a). Alternately the ribs 56 may be positioned on the exterior surface of the substrate wall 58 (FIG. 6b) or the interior surface of the substrate wall 60 (FIG. 6c).

Figure 7:
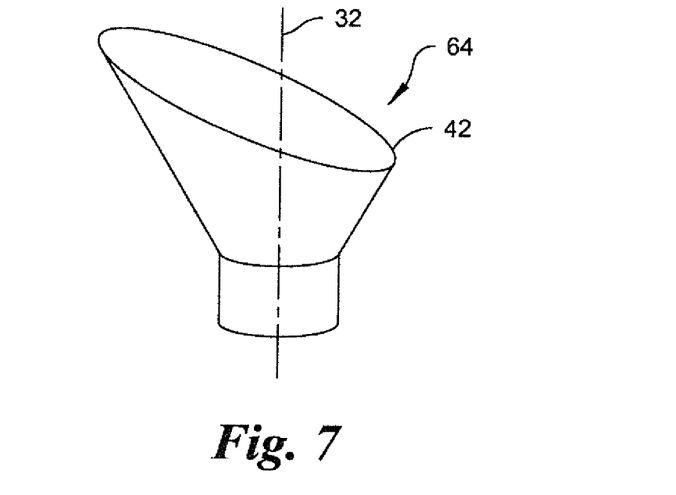
FIG. 7 is an isometric view of the sleeve adapter adapted for use with the right ventricle.

FIG. 7 represents a conical section shaped embodiment 64 of the sleeve adapter adapted for use with the right ventricle of the heart. This embodiment has a conical substrate created by cutting the substrate at an angle relative to the longitudinal axis 32 of the adapter. In this embodiment, the lip 42 of the sleeve adapter has an elliptical shape which facilitates attachment to the right ventricle.

Figure 8:
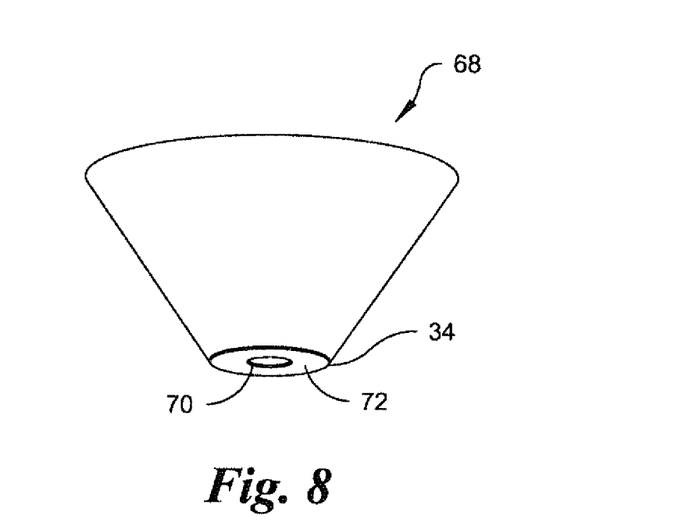
FIG. 8 is an isometric view of the sleeve adapter for use with ring attachments to a VAD pump.

FIG. 8 represents a sleeve adapter 68 adapted for use with VADs in which the opening of the substrate 34 has an attachment gasket 70 to facilitate the attachment of a VAD that utilizes an attachment gasket to attach a ventricle tube to a ventricle. In particular, a ventricle tube would be attached to this attachment gasket to provide a fluid tight connection to the VAD. Sleeve Adapter 68 may be used with a left or right ventricle as needed. The attachment gasket 70 may be made of a variety of materials known in the art including metals and alloys such as nintinol, stainless steel, titanium and various polymers and fabric materials. In one embodiment the attachment gasket is made of surgical stainless steel, nitinol, or titanium having a perimeter 72 made of a material that may be attached to the substrate 30 and bonded or otherwise attached to metal.

Figure 9:
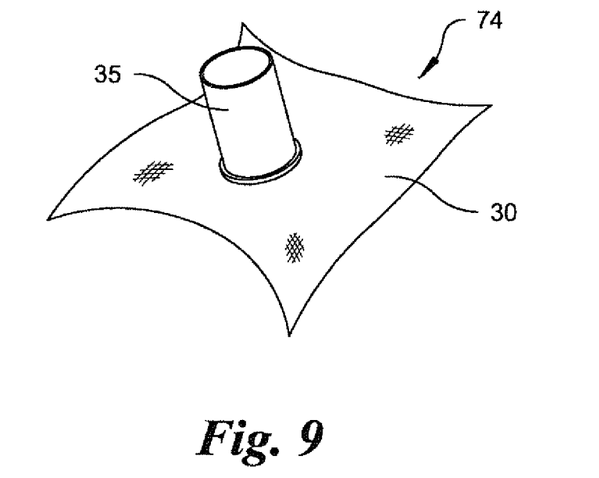
FIG. 9 is an isometric view of the sleeve adapter which can be shaped by a surgeon into a desired shape; and, FIG. 10 is an isometric view of the sleeve adapter which may be attached to the lower portion of a patient's heart.

FIG. 9 is a flexible sheet embodiment of the invention 74 in which the sleeve adapter has a substrate 30 which can be trimmed or folded by the surgeon to a desired shape to attach the sleeve adapter to a damaged ventricle. The sleeve outlet 35 may come provided pre-attached to the sleeve adapter or may be attached as needed. This embodiment allows the surgeon freedom to modify the adapter to whatever shape is needed to attach the sleeve adapter 74 to the damaged ventricle.

Figure 10:
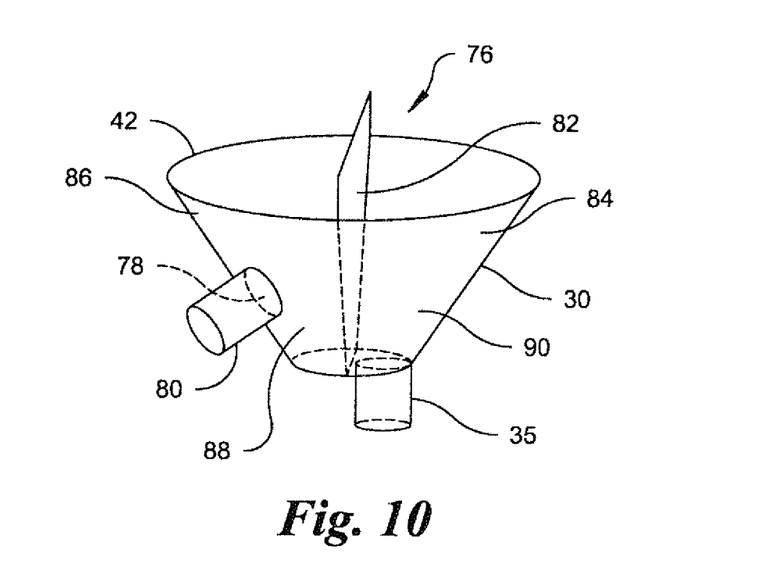

FIG. 10 provides a left and right ventricle sleeve adapter 76 that may be attached to the lower half of the heart. This sleeve adapter provides a way to attach ventricular assist devices that are able to assist both the left and right ventricles. In this embodiment the substrate has a second opening 78 and a second sleeve outlet 80. A plenum 82 is sealingly attached to the interior surface of the substrate wall. The plenum 82 separates the left side 84 from the right side 86 creating a right chamber 88 and a left chamber 90. Once a surgeon has dissected away the damaged portion of the left and right ventricles, the lip region 42 is attached to the left and right ventricles of the heart. The first and second sleeve adapters facilitate attachment to VADs that assist pumping from the left and right ventricles.

Example 1

The patient was a 66 year-old female who sustained a proximal LAD infarct in 2002. Multiple percutaneous coronary interventions (PCI) were performed without revascularization of the anterior left ventricular wall. Over the ensuing years the patient developed ischemic cardiomyopathy with marked hemodynamic compromise (LVEDd, LV EF) with a significant limitation in her activities (NYHA class IV heart failure). The patient had preserved right ventricular function (PAP, PCWP, CVP, TAPSE). Significant comorbidities include renal failure. Given her age and compromised renal function, it was felt that the patient would be better managed with a destination LVAD. After extensive discussions with the patient and husband, the decision to proceed with HeartMate II™ LVAD was made.

Following sternotomy it was evident that a large fraction of the left ventricle and apex was heavily calcified. TEE demonstrated a large amount of thrombus within the ventricular cavity. Being careful to avoid manipulation of the ventricle, to avoid embolism, the patient was placed on cardiopulmonary bypass with standard ascending aortic and right atrial dual stage cannulation. The apex was then exposed and a ventriculectomy was made. The myocardial was very calcified and friable. It was felt that sutures could not be placed with adequate hemostasis. Additionally, adequate debridement of the apical thrombus could not be perfouned through the limited ventriculectomy. At this stage, the decision was made to excise the ventricular apex and thoroughly debride all thrombus from the LV cavity. Next a ventricle assist device sleeve adapter an in-flow cannula (ventricle tube) graft was designed utilizing the standard HeartMate II™ in-flow cannula and a Dacron® graft. The Dacron® graft was sized to the diameter of the ventriculectomy. A hole the diameter of the inflow cannula was made in the center of the graft, and the cannula was inserted from the ventricular surface of the Dacron®. This cannula was secured to the Dacron® with 2-running 4-0 prolene suture lines, one on the ventricular and non-ventricular surfaces of the graft. Standard interrupted pledgeted 2-0 tevdek sutures were placed from the epicardium to endocardium circumferentially. The sutures were then passed through the Dacron® graft-inflow cannula circumferentially, from the ventricular surface. The sutures were then individually tied and the myocardium graft interface was secured with bioglue. At this stage, the HeartMate II™ LVAD can be inserted and secured in standard fashion. intra-operative TEE demonstrated good position of the inflow cannula. The patient had an uneventful post-operative recovery and was discharged to rehab without incident. She did not suffer any neurologic events.

The invention claimed is:

1. A sleeve adapter for connecting a ventricular assist device to a ventricle of a heart having a ventricular surface, said sleeve adapter comprising:
a flexible substrate having an opening therethrough;
a sleeve outlet extending axially through said opening in said substrate, said sleeve outlet having first and second ends oppositely disposed, said substrate being sealingly attached to said sleeve outlet; wherein
said substrate is adapted for sealing attachment to said ventricular surface, said first end of said sleeve outlet facing said ventricle, said second end of said sleeve outlet projecting outwardly from said ventricle and being connectable in fluid communication with said ventricular assist device, wherein blood travels from said ventricle to said ventricular assist device.

2. The sleeve adapter according to claim 1, wherein said substrate has a conical shape.

3. The sleeve adapter of claim 2, wherein said conical shaped sleeve adapter has a lip defining an opening.

4. The sleeve adapter of claim 3, wherein said lip is elliptical.

5. The sleeve adapter of claim 1, wherein said substrate is sealingly attached to said sleeve outlet at one end thereof.

6. The sleeve adapter of claim 1, wherein said substrate is sealingly attached to said sleeve outlet between said first and second ends of said sleeve outlet.

7. The sleeve adapter according to claim 1, wherein said substrate is made from a material selected from the group consisting of polytetrafluoroethylene (PTFE), gelatin sealed grafts, antibiotic treated grafts, velour, a porous form of polytetrafluoroethylene, polyethylene terepthalate, silk and combinations thereof.

8. The sleeve adapter according to claim 1, wherein said sleeve outlet is made from a material selected from the group consisting of polytetrafluoroethylene (PTFE), gelatin sealed grafts, antibiotic treated grafts, velour, a porous form of polytetrafluoroethylene, polyethylene terepthalate, silk and combinations thereof.

9. The sleeve adapter of claim 1, further comprising a rib attached to said substrate.

10. The sleeve adapter of claim 9, wherein said rib extends helically around said substrate.

11. The sleeve adapter of claim 9, wherein said rib extends circumferentially around said substrate.

12. The sleeve adapter of claim 9, wherein said rib is detachable.

13. The sleeve adapter of claim 9, wherein said substrate comprises a cone, and said rib extends lengthwise along said cone.

14. The sleeve adapter of claim 1, wherein said substrate has markings to facilitate cutting said substrate to a desired size.

15. A sleeve adapter for connecting a ventricular assist device to a ventricle of a heart having a ventricular surface, said sleeve adapter comprising:
a flexible substrate having an opening,
an attachment gasket attached to said opening in said substrate,
said attachment gasket being connectable in fluid communication with said ventricular assist device, wherein blood travels from said ventricle to said ventricular assist device.

16. The sleeve adapter according to claim 1, further comprising sutures extending between said sleeve outlet and said substrate for attaching said substrate to said sleeve outlet.

17. The sleeve adapter according to claim 1, further comprising sutures extending between said substrate and said ventricle for attaching said substrate to said ventricle.

18. The sleeve adapter of claim 1, said heart having left and right ventricles, said left and right ventricles having ventricle surfaces, further comprising said substrate having a second opening therethrough and a second sleeve outlet in a spaced relation from said sleeve outlet and said second sleeve outlet extending through said substrate,
said second sleeve outlet having first and second ends oppositely disposed, said substrate being sealingly attached to said second sleeve outlet,
said second sleeve outlet projecting outward from a ventricle and being connectible in fluid communication with a ventricular assist device,
said substrate having a wall,
a plenum attached to the interior surface of the substrate wall of said substrate, said plenum dividing said substrate into a first chamber and a second chamber,
said first chamber sealingly attachable to said left ventricle,
said second chamber sealingly attachable to said right ventricle.

* * * * *